(12) United States Patent
Earthman et al.

(10) Patent No.: US 7,008,385 B2
(45) Date of Patent: Mar. 7, 2006

(54) EVALUATION OF REFLECTED TIME-ENERGY PROFILE FOR EVALUATION OF OSSEOINTEGRATION AND DENSITY

(76) Inventors: James C. Earthman, 6 Virgil Ct., Irvine, CA (US) 92612; Cherilyn G. Sheets, 22 Hermitage La., Newport Beach, CA (US) 92660

( * ) Notice: Subject to any disclaimer, the term of this patent is extended or adjusted under 35 U.S.C. 154(b) by 0 days.

(21) Appl. No.: 10/802,117

(22) Filed: Mar. 16, 2004

(65) Prior Publication Data
US 2004/0249304 A1    Dec. 9, 2004

Related U.S. Application Data

(63) Continuation-in-part of application No. 10/671,002, filed on Sep. 25, 2003.

(60) Provisional application No. 60/414,691, filed on Sep. 27, 2002, provisional application No. 60/422,186, filed on Oct. 29, 2002.

(51) Int. Cl.
*A61B 5/103* (2006.01)
*A61B 19/00* (2006.01)

(52) U.S. Cl. .............. 600/590; 600/553; 73/12.01; 433/72

(58) Field of Classification Search .............. 600/587, 600/553, 552, 589, 590; 73/12.01, 573, 579; 433/72, 215; 33/513
See application file for complete search history.

(56) References Cited

U.S. PATENT DOCUMENTS

| | | | |
|---|---|---|---|
| 3,722,100 A | 3/1973 | Weisman et al. | |
| 4,341,519 A | 7/1982 | Kuhn et al. | |
| 4,482,324 A | 11/1984 | Wohlgemuth | |
| 4,499,906 A | 2/1985 | Wohlgemuth et al. | |
| 4,689,011 A | 8/1987 | Wohlgemuth | |
| 4,764,114 A | 8/1988 | Jeffcoat et al. | |
| 5,144,753 A | 9/1992 | Murphy | |
| 5,318,442 A | 6/1994 | Jeffcoat et al. | |
| 5,518,008 A | 5/1996 | Cucchiaro et al. | |
| 6,120,466 A | 9/2000 | Earthman | |

OTHER PUBLICATIONS

Marc E. Levenston & Dennis R. Carter, "An Energy Dissipation-Based Model for Damage Stimulated Bone Adaptation", *Journal of Biomechanics*, vol. 31 (1998), pp. 579-586.

W. Schulte, B. d'Hoedt, D. Lukas, M. Maunz and M. Steppler "Periotest for Measuring Periodontal Characteristics-Correlation with Periodontal Bone Loss", *Journal of Periodontal Research*, 1992, vol. 27, pp. 184-190.

(Continued)

*Primary Examiner*—Charles Marmor
(74) *Attorney, Agent, or Firm*—Knobbe, Martens, Olson & Bear LLP

(57) ABSTRACT

A method for measuring the acoustic damping capacity of a material or structure, such as a layered honeycomb structure, comprises tapping the honeycomb structure with a tapping rod. The tapping action imparts mechanical energy to the honeycomb structure. The method further comprises measuring, for a time interval, energy reflected from the honeycomb structure as a result of the tapping. The method further comprises creating a time-energy profile based on the energy reflected from the honeycomb structure during the time interval. The method further comprises evaluating the time-energy profile to determine the acoustic damping capacity of the honeycomb structure.

8 Claims, 9 Drawing Sheets

OTHER PUBLICATIONS

A. Barzin, C.G. Sheets and J.C. Earthman "Mechanical Biocompatibility of Dental Implant Materials", Proceedings of the Fourth Pacific Rim International Conference on materials, Japanese Institute of Metals, pp. 2492-2952 (2002).

Ichiro Owan, David B. Burr, Charles H. Turner, Jinya Qiu, Yuan Tu, Jude E. Onyia, and Randall L. Duncan "Mechanotransduction in Bone: Osteoblasts are More Responsive to Fluid Forces than Mechanical Strain", *The American Physiological Society* (Sep. 1997), vol. 273, pp. C810-C815.

Cherilyn G. Sheets, DDS. and James C. Earthman, Ph.D., "Natural Tooth Intrusion and Reversal in Implant-Assisted Prosthesis: Evidence of and a Hypothesis for the Occurrence", *The Journal of Prosthetic Dentistry*, Dec. 1993, vol. 70, No. 6, pp. 513-520.

D. Lukas, "Periotest: Dynamically Diagnosing the Human Periodontium and the Dental Implant-Bone Interface", http://www.periotest.de/beschreibung.htm, website dated Jul. 4, 2002.

Cherilyn G. Sheets, DDS. and James C. Earthman, Ph.D., "Tooth Intrusion in Implant-Assited Protheses", *The Journal of Prosthetic Dentistry*, Jan. 1997, vol. 77, No. 1, pp. 39-45.

J.R. Davis, et al., Metals Handbook, vol. 17, (Metals Park, OH; ASM International, 1989), 241-244.

M.F. Ashby, "MaterialsSelection in Mechanical Design", (New York; Pergamon Press, 1992), 40.

A.B. Strong, *Fundamentals of Composites Manufacturing: Materials, Methods, and Applications*, Society of Manufacturing Engineers (1989), 92.

K.K. Chawla, *Composite Materials Science and Engineering*, (New York: Springer-Verlag, 1987), 229-258.

B.J. Lazan, "Damping of Materials and Members in Structural Mechanics", Pergamon Press, New York (1968).

J. Zhang, et al., "Effects of Secondary Phases on the Damping Behavior of Metals, Alloys and Metal Matrix Composites", Materials Science and Engineering Reviews, R13, No. 8, Dec. 1994.

S. Kalpakjian, "Manufacuring Engineering and Technology", Addison-Wesley (1992).

D.A. Brenner et al., "Novel Instrumentation for Quantitive Determination of Energy Damping in Materials and Structures", Scripta Metallurgica et Materialia, vol. 13, No. 4, pp. 467-470, 1994.

Operating Instructions for "PERIOTEST—for you by Siemens", Siemens Corporation, pp. 1-11.

E.J. Graesser et al. Reprt No1 DTRC-SME-91/05, David Taylor Research Center, Annapolis, Maryland (1991).

B.D. Stanley, et al. "Nondestructive Evaluation and Materials Properties III, The Minerals, Metals Materials Society", 1997.

EVALUATION OF REFLECTED TIME-ENERGY PROFILE FOR EVALUATION OF OSSEOINTEGRATION AND DENSITY

PRIORITY APPLICATIONS

This application is a continuation-in-part of application Ser. No. 10/671,002 (filed 25 Sep. 2003), which claims the benefit of U.S. Provisional Application 60/414,691 (filed 27 Sep. 2002), and U.S. Provisional Application 60/422,186 (filed 29 Oct. 2002). The entire disclosure of both all of these priority applications is hereby incorporated by reference herein.

FIELD OF THE INVENTION

The present invention relates generally to evaluation of the mechanical properties of an object, and more specifically relates to evaluation of a time-energy profile response from the object after an impact thereon.

BACKGROUND OF THE INVENTION

When an object is subjected to an impact force, a stress wave is transmitted through the object. This stress wave causes deformations in the internal structure of the object. As the object deforms it acts, in part, as a shock absorber, dissipating a portion of the mechanical energy associated with the impact. The ability of the object to dissipate mechanical energy, commonly referred to as the "damping capacity" of the object, depends on several factors, including the type and structural integrity of the materials comprising the object.

Instruments have been developed that are capable of quantitatively measuring the damping capacity of an object. An example of such an instrument is described in U.S. Pat. No. 6,120,466 ("the '466 patent"), issued 19 Sep. 2000 and entitled "System and Method for Quantitative Measurements of Energy Damping Capacity," the entire disclosure of which is hereby incorporated by reference herein. The instrument disclosed in the '466 patent provides an objective, quantitative measurement of the damping capacity of an object, referred to as the loss coefficient 17. The energy of an elastic wave attenuates relatively quickly in materials with a relatively high loss coefficient, whereas the energy of an elastic wave attenuates relatively slowly in materials with a relatively low loss coefficient.

The damping capacity of an object is an important parameter in a wide variety of applications. For example, in the field of dentistry, when a healthy tooth is subjected to an impact force, the mechanical energy associated with the impact is primarily dissipated by the periodontal ligament. Changes in the structure of the periodontal ligament that reduce its ability to dissipate the mechanical energy associated with an impact force, and thus reduce overall tooth stability, can be detected by measuring the loss coefficient of the tooth.

SUMMARY OF THE INVENTION

While evaluation of the loss coefficient provides a quantitative parameter corresponding to the damping capacity of an object, the loss coefficient alone does not provide complete information regarding the structural integrity of an object. Additional information can be provided by evaluating the time-energy profile as the object is subjected to an impact force. For example, materials that deform uniformly will exhibit a time-energy profile having a smooth, symmetric, bell shape. In contrast, nonuniform materials or materials having internal defects will cause the time-energy profile to be asymmetric.

In accordance with the foregoing, in one embodiment of the present invention, a method for measuring the acoustic damping capacity of a layered honeycomb structure comprises tapping the honeycomb structure with a tapping rod. The tapping action imparts mechanical energy to the honeycomb structure. The method further comprises measuring, for a time interval, energy reflected from the honeycomb structure as a result of the tapping. The method further comprises creating a time-energy profile based on the energy reflected from the honeycomb structure during the time interval. The method further comprises evaluating the time-energy profile to determine the acoustic damping capacity of the honeycomb structure.

According to another embodiment of the present invention, a method for measuring the damping capacity of a prosthetic dental implant structure to determine the stability of the implant structure comprises tapping the implant structure with a tapping rod. The tapping action imparts mechanical energy to the implant structure. The method further comprises measuring, for a time interval, energy reflected from the implant structure as a result of the tapping. The method further comprises creating a time-energy profile based on the energy reflected from the implant structure during the time interval. The method further comprises evaluating the time-energy profile to determine the damping capacity of the implant structure.

According to another embodiment of the present invention, a method for measuring the damping capacity of a tooth to assess the tooth health comprises tapping the tooth with a tapping rod. The tapping action imparts mechanical energy to the tooth. The method further comprises measuring, for a time interval, energy reflected from the tooth as a result of the tapping. The method further comprises creating a time-energy profile based on the energy reflected from the tooth during the time interval. The method further comprises evaluating the time-energy profile to determine the damping capacity of the tooth.

According to another embodiment of the present invention, a method for determining a damping capacity of an object comprises tapping the object with a tapping rod. The tapping action imparts mechanical energy to the object. The method further comprises measuring, for a time interval, energy reflected from the object as a result of the tapping. The method further comprises creating a time-energy profile based on the energy reflected from the object during the time interval. The method further comprises evaluating the time-energy profile to determine the damping capacity of the object.

According to another embodiment of the present invention, a method comprises tapping an object, thereby imparting mechanical energy to the object. The method further comprises measuring energy reflected from the object as a result of the tapping. The method further comprises creating a time-energy profile of the energy reflected from the object. The method further comprises evaluating the time-energy profile to make a determination regarding the structural characteristics of the object.

According to another embodiment of the present invention, a system for providing information regarding the damping capacity of an object comprises a test probe housing a movable impact rod. The test probe is mounted against the object. The system further comprises an accelerometer configured to detect energy reflected from the object after the impact rod impacts the object. The system further comprises a computer coupled to the accelerometer. The computer is configured to generate and display a time-energy profile of the reflected energy as detected by the accelerometer.

BRIEF DESCRIPTION OF THE DRAWINGS

Exemplary embodiments of the damping capacity evaluation system are illustrated in the accompanying drawings, which are for illustrative purposes only. The drawings comprise the following figures, in which like numerals indicate like parts.

DETAILED DESCRIPTION OF PREFERRED EMBODIMENTS

The systems described herein comprise hardware and virtual instrumentation software capable of analyzing the energy dissipation characteristics of a specimen. The energy dissipation information provided by these systems and methods provides objective information that is relevant to the evaluation and design of a wide variety of mechanical structures, such as natural and prosthetic dental structures and engineering structures. Such information is also useful in the study of materials and composites.

Figure 1:
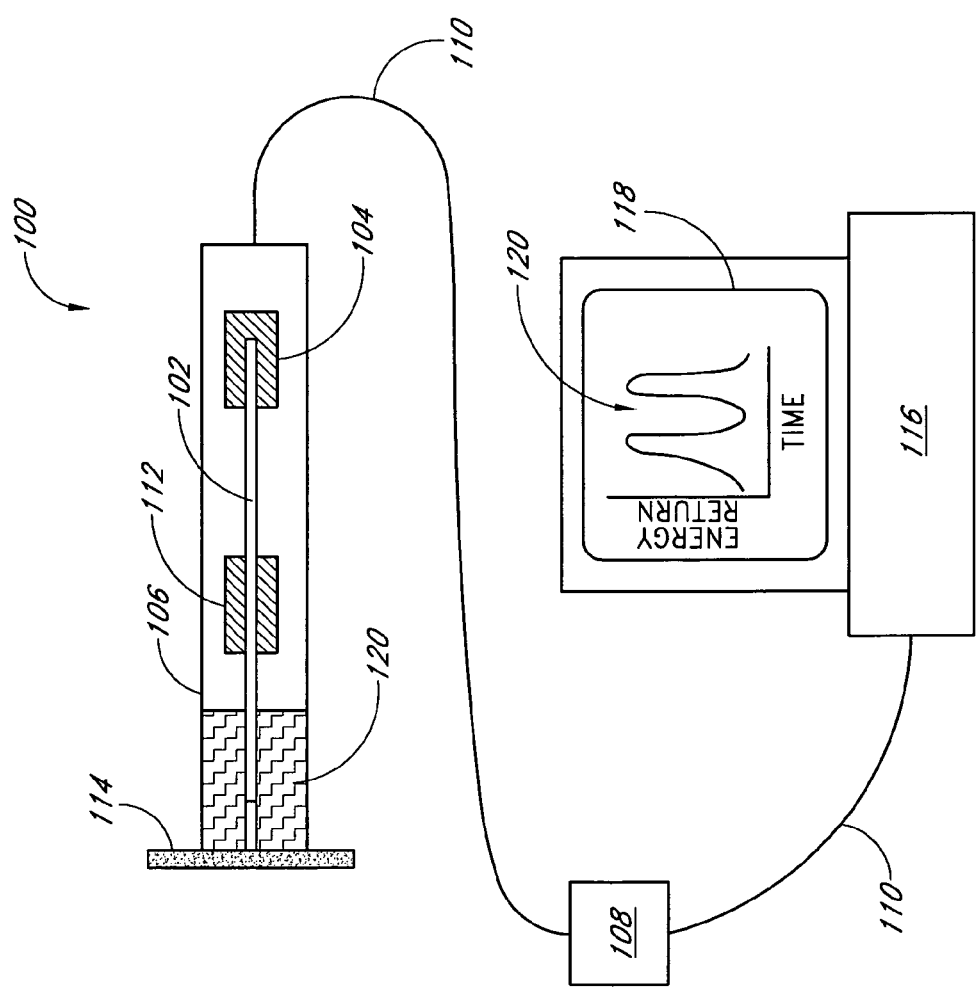
FIG. 1 is a schematic illustration of an exemplary energy dissipation test system.

An exemplary energy dissipation test system is illustrated in FIG. 1. This system comprises a percussion instrument 100 having a movable tapping rod 102 mounted within a housing 106. In one embodiment, the percussion instrument 100 comprises a Periotest®, available from Medizintechnik Gulden AG (Bensheim, Germany). In a modified embodiment, the percussion instrument comprises a Periotest® that has been modified as described in the '466 patent, thereby allowing more accurate and reproducible measurements to be performed. For example, outfitting the Periotest® with a polytetrafluoroethylene ("PTFE") sleeve 120 configured to be placed against a specimen 114 can increase the accuracy and reproducibility of measurements. In other embodiments, other types of percussion instrumentation can be used.

Still referring to FIG. 1, the percussion instrument 100 is configured to be placed against a specimen 114 for which energy dissipation analysis is to be performed. To test the specimen 114, the tapping rod 102 is impacted against the specimen 114 one or more times. For example, in one embodiment, the tapping rod impacts the specimen 114 approximately sixteen times in a period of four seconds. In other embodiments, faster or slower impact repetition rates are used. In an exemplary embodiment, the tapping rod 102 is driven by one or more propulsion coils 112 electronically activated by a finger switch (not shown), although the propulsion coils 112 can be activated remotely in other embodiments.

When the tapping rod 102 impacts the specimen 114, some of the kinetic energy of the tapping rod 102 is converted to mechanical energy propagating through the specimen 114 as a stress wave. Most of the remaining of the kinetic energy is converted (dissipated) to heat, as dictated by the loss coefficient and structure of the specimen. A portion of the propagated mechanical energy is reflected back to the tapping rod 102, where it can be detected by an accelerometer 104 mounted within the housing 106. The accelerometer 104 produces signals that correspond to the reflected mechanical energy resulting from the impact between the tapping rod 102 and the specimen 114.

Still referring to the exemplary embodiment illustrated in FIG. 1, the signals generated by the accelerometer 104 are provided to a data acquisition board housed in a computer 116 via an instrumentation interface 108. In one embodiment, the instrumentation interface 108 comprises a signal conditioner and an independent power supply. In a modified embodiment, the instrumentation interface is incorporated within the computer. In an exemplary embodiment, the data acquisition board comprises a sixteen bit analog to digital converter channel. In such embodiments, the computer 116 operates at a sampling rate of at least about 800 kHz; although in other embodiments, the computer 116 operates at a sampling rate of at least about 500 kHz. The signals can be transmitted from the accelerometer 104 to the computer 116 via a coaxial cable 110, or via another signal transport mechanism.

In the illustrated embodiment, the computer 116 includes virtual instrumentation software capable of analyzing the signals received from the accelerometer 104. A wide variety of different types of data acquisition software can be used to acquire data from the accelerometer 104. In one embodiment, customized data acquisition software developed using the LabVIEW programming environment, available from National Instruments (Austin, Tex.), is used, although other programming environments can be used in other embodiments.

After the signals are received from the accelerometer 104, the data processing software is capable of quantitatively measuring the damping capacity of the specimen 114, which is often expressed in terms of the loss coefficient 17. For a series of impacts, as described above, several calculations of the damping capacity can be performed. For example, in one embodiment the tapping rod 102 impacts the specimen 114 sixteen times, and the damping capacity of the specimen is calculated for ten of the sixteen impacts. In such embodiments, the standard deviation of the damping capacity measurements can be calculated, thereby providing the user with an indication of the accuracy of the measurements. Specifically, if the percussion instrument 100 was not properly aligned with the specimen 114, or if another source of error was introduced into the measurement process, this error will likely manifest itself in the form of a elevated standard deviation of a series of damping capacity measurements.

Further discussion of the loss coefficient and methods for its calculation based on data generated by percussion instrumentation, including details on method for calibrating percussion instrumentation, can be found in the '466 patent.

Still referring to the exemplary embodiment illustrated in FIG. 1, the computer 116 further comprises memory registers, such that the amount of energy reflected from the specimen 114 at several points over a discrete time period can be recorded. In such embodiments, the energy returned from the specimen 114 can be plotted as a function of time on a display 118 attached to the computer 116. This configuration allows the user to view and analyze the time-energy profile 120 of the energy reflected from the specimen 114.

In addition to generation of a time-energy profile 120, other analyses can also be performed on the signals returned from the accelerometer 104. For example, the amount of work W associated with the impact can be evaluated by integrating the force F applied to the tapping rod 102 with respect to the displacement of the specimen $u_s$. That is, $$W = \int F \cdot du_s.$$

The force F applied to the tapping rod 102 during its impact with the specimen 114 can be measured using the accelerometer 104. After the impact, the amount of work W depends partially on the quantity of defects present in the specimen 114. In particular, defects in the specimen 114 dissipate the kinetic energy of the rod as it impacts the specimen 114, thereby reducing the amount of elastic energy available to be returned to the tapping rod 102. A comparison of the amount of elastic energy returned to the tapping rod 102 and the total work W associated with the impact can be used to determine the quantity and nature of structural defects present in the specimen 114.

Exemplary Application: Natural and Prosthetic Dental Structures.

As described above, the mechanical energy associated with an impact against a natural tooth is primarily dissipated by the periodontal ligament. More specifically, when a tooth is subjected to an impact force, a stress wave is transmitted through the tooth and into the periodontal ligament, which functions to connect the tooth to the underlying bone. Because of the way it deforms, the periodontal ligament acts as a shock absorber, dissipating much of the energy associated with the impact. This damping process advantageously reduces the resultant impact force transmitted to the surrounding bone. In contrast, dental implant prostheses often have no mechanism by which to dissipate significant amounts of mechanical energy because of the nature of the materials used. Thus, mechanical energy tends to pass from an implant structure to the underlying bone with relatively little damping. This difference in mechanical behavior may be particularly critical for people who habitually brux and/or clench their teeth, since such behavior imparts relatively large impact forces on teeth.

The relative extent to which a material dissipates elastic mechanical energy can be characterized using the loss coefficient 17, as discussed previously. Loss coefficient values have been determined for natural teeth, as well as for a wide variety of implant-supported superstructures, such as superstructures made of resin matrix composites, gold alloys, and porcelain fused to gold laminates. Implant-supported structures typically dissipate less mechanical energy than their natural tooth counterparts. However, the ability of an implant to dissipate mechanical energy depends on the level of osseointegration around the implant: poor osseointegration between an implant and the surrounding bone can cause abnormally high levels of energy dissipation.

Thus, energy dissipation initially increases after placing an implant, but then usually decreases as osseointegration progresses. Eventually, the energy dissipation (damping) capacity of the implant becomes constant as the osseointegration process progresses to completion.

Healthy teeth and well-integrated implants exhibit a low level of energy dissipation with a smooth, symmetric, bell-shaped time-elastic energy profile. As used in this context, the term "elastic energy" refers to the elastic energy imparted to the tapping rod 102 of the percussion instrument 100. The elastic energy $E_e$ is given by $E_e = k \cdot F^2$, where the constant k varies inversely with the effective elastic modulus of the tapping rod 102 and where the force F is proportional to both the mass of the tapping rod 102 and the maximum deceleration of the tapping rod 102 as a result of the stress wave created from the impact.

Figure 2:
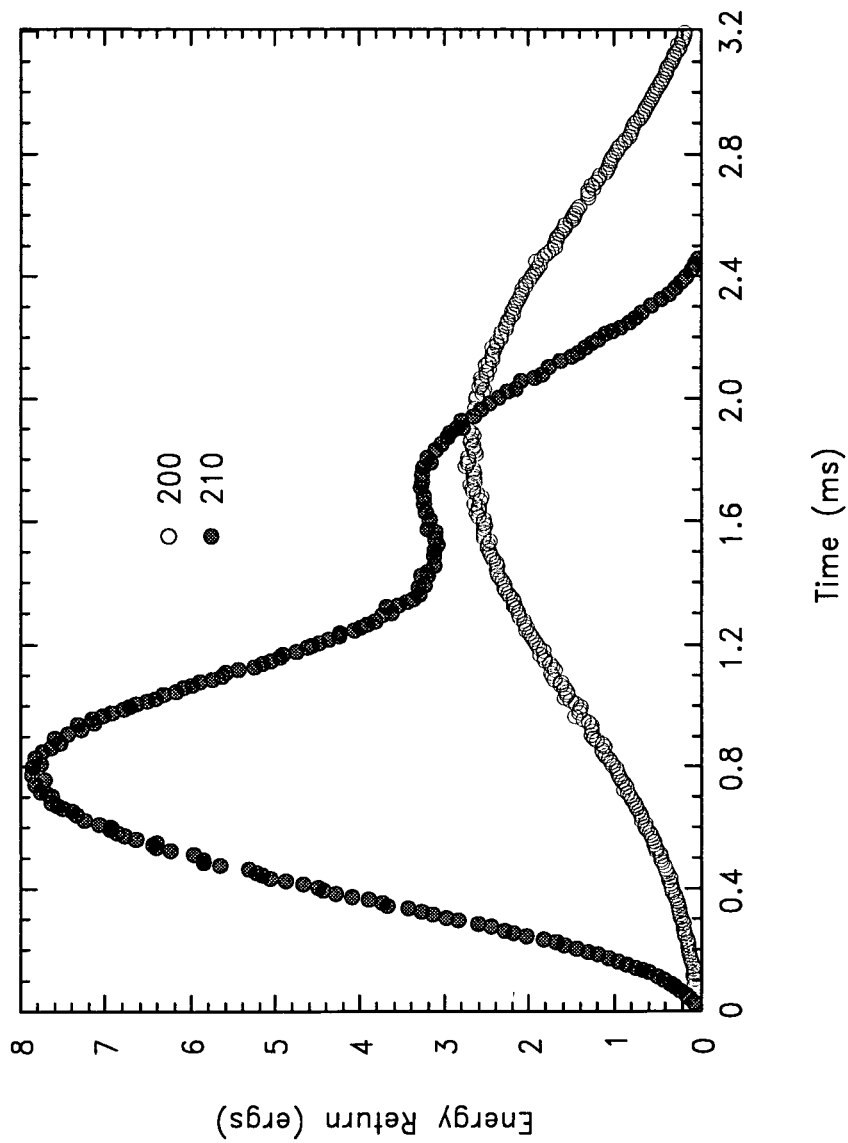
FIG. 2 illustrates time-energy profiles for a healthy tooth (200) and an implant that is not well-integrated (210).

In contrast to well-integrated implants, implants suffering from poor osseointegration, bone loss, internal defects, or a damaged structure will typically exhibit a nonuniform time-energy profile. For example, FIG. 2 illustrates a "normal" time-energy profile 200 for a healthy tooth, as well as an "abnormal" time-energy profile 210 for an implant structure that is not well-integrated. As illustrated, the time-energy profile 200 for the healthy tooth has a smooth, symmetric, bell shape, whereas the time-energy profile 210 for the abnormal implant structure is not smooth and symmetric, and has a secondary maxima 212. The shape of the time-energy profile for the abnormal implant structure indicates that defects, such as loose screws, a damaged internal structure, bone loss at the bone/implant interface, or poor osseointegration, are present. In addition to secondary maxima, other abnormalities in the shape of the time-energy profile that are indicative of structural defects include scattered data, asymmetries and irregular shapes.

Figure 3:
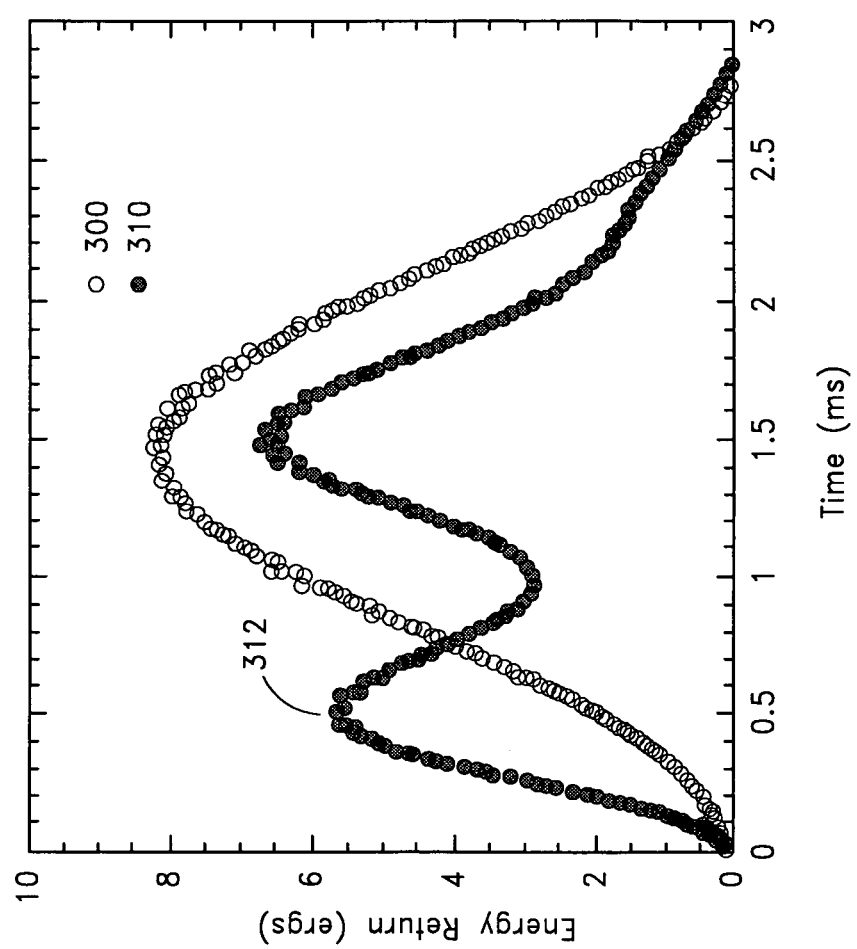
FIG. 3 illustrates time-energy profiles for a well-integrated implant (300) and an implant that is not well-integrated (310).

An additional example of this principle is provided in FIG. 3, which illustrates a "normal" time-energy profile 300 of a well-integrated implant, as well as an "abnormal" time-energy profile 310 for an implant structure that is not well-integrated. Both of these implant structures are located in the mouth of a heavily parafunctional elderly patient. As explained previously, the presence of the secondary maxima 312 indicates that defects, such as loose screws, a damaged internal structure, bone loss at the bone/implant interface, or poor osseointegration, are present at the implant site.

The reflected time-energy profile provides information about the stability of the tooth or implant in the underlying anatomy. For example, in one embodiment an assessment of bone density of the bone surrounding the tooth or implant can be made based on an evaluation of the reflected time-energy profile. The bone density assessment can be quantitative or qualitative. In such embodiments, an assessment of bone density can provide an early indication of the stability of an implant shortly after implantation, and before significant osseointegration occurs. In other embodiments, the reflected time-energy profile is used to evaluate the health of the tooth or implant, as well as surrounding tissue, including the periodontal ligament and/or bone.

In accordance with the foregoing, it will be appreciated that the reflected time-energy profile can be used to assist in the diagnosis or assessment of a variety of medical conditions, including medical conditions related to the dental anatomy. For example, the reflected time-energy profile can be used to assist in the diagnosis of trauma-induced tooth fractures and of bone loss due to abscesses. Likewise, the results of bone augmentation surgeries can be assessed in a similar manner.

The foregoing examples illustrate that analysis of the time-energy profile of a dental structure can provide information about the integrity and stability of that structure. The term "dental structure" is used broadly in this context, and refers to natural teeth and prosthetic implants, as well as the bone and ligament structures that anchor such objects within the human body. These analysis techniques provide clinicians with an accurate, fast and simple tool that provides information on the stability of natural and prosthetic dental structures without requiring an invasive procedure. In other embodiments, the integrity and stability of other medical devices and anatomical structures, such as orthopedic implants and Prosthetic implants, can be evaluated based on an assessment of a reflected time-energy profile.

Exemplary Application: Composite Structures.

The percussion instrumentation described above can also be used in fields other than dentistry. For example, such instrumentation can be used in assessing the local damping capacity of composite structures, such as layered honeycomb composites. In particular, use of such instrumentation in the testing of composite structures advantageously allows the damping capacity of these structures to be evaluated without damaging the structures. The instrumentation disclosed herein is also light, portable, easy to use, quick and inexpensive as compared to conventional apparatuses for evaluating damping capacity.

Because damping capacity measures the ability of a material to absorb and isolate vibration, damping capacity is of particular interest with respect to materials used for acoustic insulation, such as in the aerospace, boating, civil engineering and automotive engineering fields. Thus it is often sought to test the damping capacity of new materials under development, as well as conventional materials after sustained use.

Figure 7:
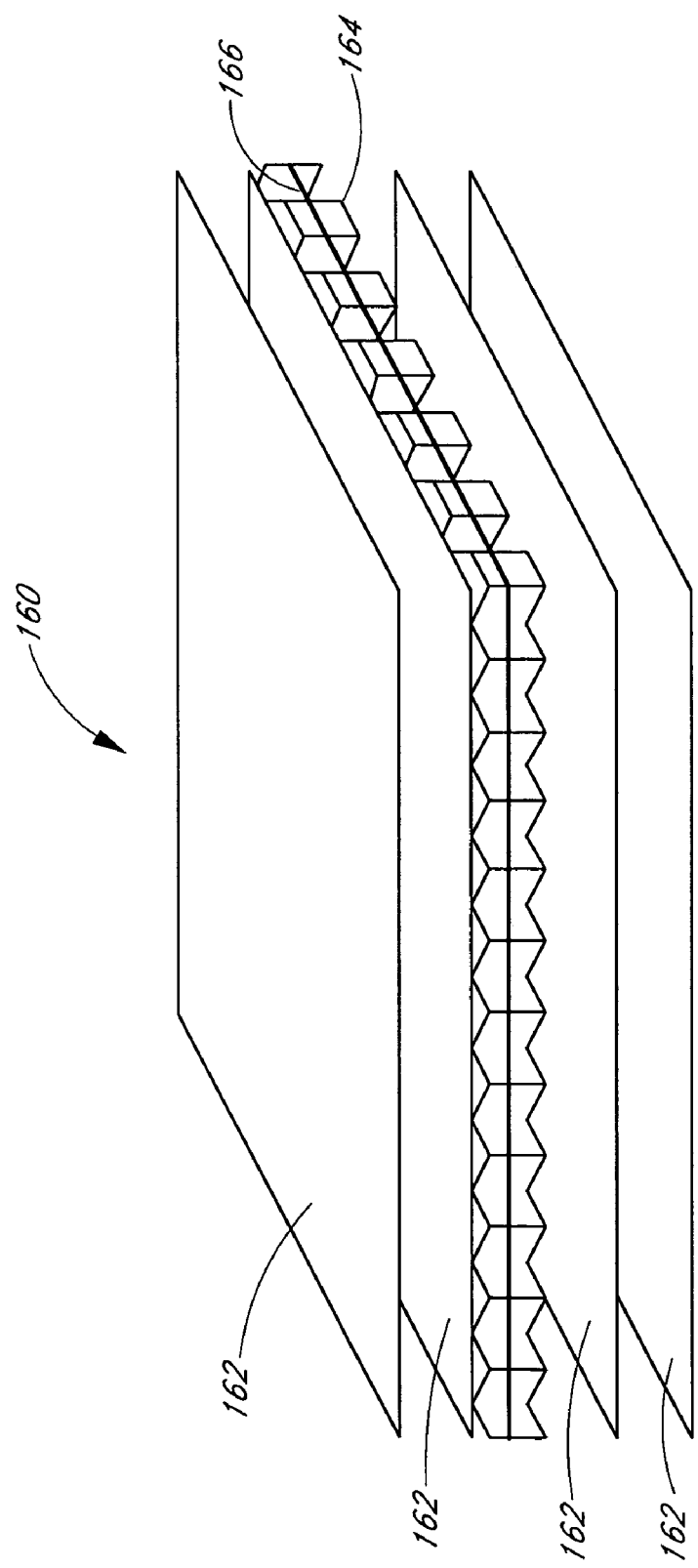
FIG. 7 is an exploded perspective view of an exemplary layered composite honeycomb material.

As an example, layered honeycomb structures generally have a relatively high damping capacity, and thus are often used as acoustic insulators in these fields. An exemplary layered honeycomb composite structure 160 is illustrated in FIG. 7. The exemplary layered honeycomb composite structure 160 includes one or more relatively thin facings 162 that have high strength and stiffness. The facings enclose a honeycomb core structure 164 that is relatively thick, but lightweight and with high strength in the direction perpendicular to the facings. For example, the honeycomb core structure 164 can comprise a Nomex® honeycomb core, available from E.I. du Pont de Nemours and Company (Wilmington, Del.). The facings 162 and the core 164 are generally bonded together, either mechanically or with adhesives (such as, for example, with a phenolic resin), thus giving the structure 160 composite properties. In the composite structure 160, the facings 162 carry bending stresses, while the core 164 carries shear stresses. When exposed to acoustic vibrations for a prolonged period, degradation in the bonds between the layers, as well as in the honeycomb core 164 itself, can cause a layered honeycomb core structure 160 to have diminished acoustic insulation capacity.

As illustrated in FIG. 7, the composite structure 160 optionally includes an inner damping core 166 incorporated into the honeycomb core structure 164. While inclusion of the damping core 166 can increase the weight of the composite structure 160, it can cause a significant increase in the damping capacity of the composite structure 160. For example, in one embodiment, addition of the damping core 166 to the composite structure 160 increases the damping capacity of the composite structure by approximately 65%. In a modified embodiment, the damping core 166 is selectively included in the composite structure 160, such that vibration isolation can be targeted to a particular portion of the composite structure 160 without significantly increasing the weight of the composite structure 160.

In addition to having a relatively high damping capacity, honeycomb structures, including layered honeycomb structures offer several other advantages. For example, such structures generally have a high strength to weight ratio, are resistant to corrosion, and can be configured to be electrically conductive or insulating, depending on the requirements of a particular application. Furthermore, these structures can be made fire resistant by using an appropriate resin and can be molded into complex shapes.

Figure 4:
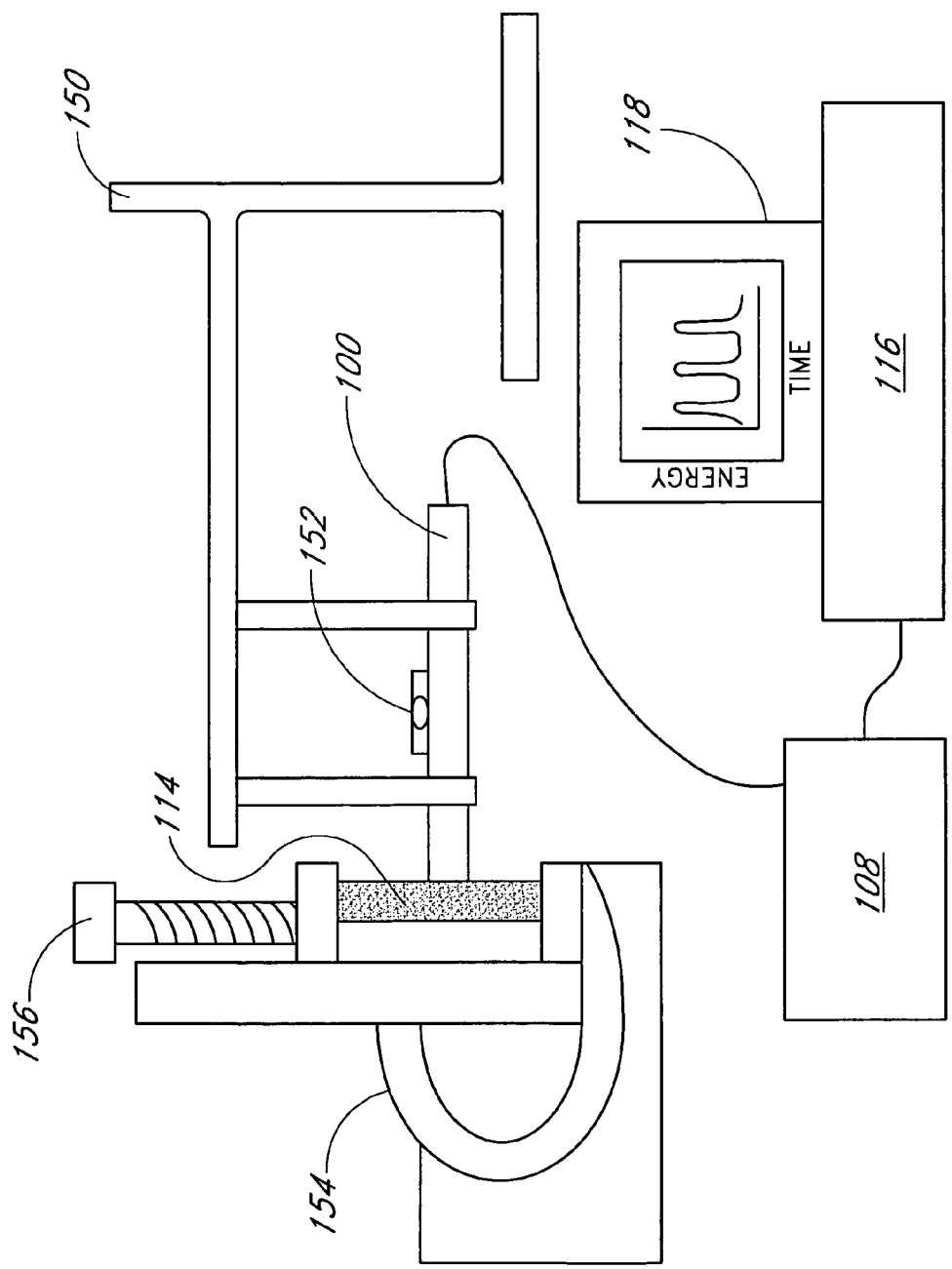
FIG. 4 illustrates an exemplary embodiment of an apparatus configured for evaluating the damping capacity of composite structures.

Referring now to FIG. 4, an exemplary embodiment of an apparatus configured for evaluating the damping capacity of composite structures is illustrated. The apparatus comprises a percussion instrument 100 mounted within a secured bracket 150 configured to stabilize the percussion instrument 100. The percussion instrument 100 is optionally outfitted with a level 152 to assist in aligning the percussion instrument 100 substantially perpendicular to a specimen 114 that is to be tested. In an exemplary embodiment, the specimen 114 is mounted in an angle vise 154 having a hand-adjustable vise drive 156, thereby allowing the specimen 114 to be held in compression during testing. In a modified embodiment, the angle vise 154 is outfitted with rubber grips to reduce external sources of vibrational noise that could be detected by the percussion instrument 100.

Still referring to FIG. 4, and similar to the configuration illustrated in FIG. 1, the percussion instrument 100 is electronically connected to a computer 116 via an instrumentation interface 108. In such embodiments, the computer 116 comprises a display 118 capable of graphically presenting data generated by the percussion instrument 100, such as a time-energy profile.

The testing apparatus illustrated in FIG. 4 can be used to evaluate the damping capacity of a wide variety of materials, including structures used for damping, shock absorbance, and impact resistance. For example, in one application, this apparatus can be used to evaluate the damping capacity of layered honeycomb composite specimens. In such an application, the specimen 114 to be tested is mounted in the angle vise 154, which is tightened using the vise drive 156 to a torque of approximately 2765 g•cm, although in other embodiments, the specimen 114 can be loaded to a different torque. In other embodiments, the testing apparatus can be configured to evaluate other materials, such as electronic packaging materials and other electronic components.

The percussion instrument 100 is then positioned at approximately the center of the specimen 114 in an orientation that is approximately perpendicular to one of the outer facings of the specimen 114. As described above, in certain configurations, a level can be used to assist in aligning the percussion instrument 100 and the specimen 114 in a substantially perpendicular orientation. In one embodiment, the end of the percussion instrument 100 that is placed against the specimen 114 comprises a Teflon® tip having a diameter of approximately 2.5 cm. This design aids in aligning the specimen 114 with the percussion instrument 100, as well as in reducing external sources of vibrational noise that could be detected by the percussion instrument 100.

As described above, the percussion instrument 100 is configured to impact a tapping rod against the specimen 114. In one testing configuration, the tapping rod impacts the specimen 114 sixteen times in four seconds, with each impact causing vibrational energy to be reflected back to the tapping rod, where it is detected by the accelerometer, which generates a signal that is sent to the computer 116. The computer 116 can be configured to analyze the reflected energy associated with all or a portion of the impacts. For example, in one testing configuration, the computer 116 analyzes the reflected energy for ten of the sixteen impacts. The computer analysis can comprises analysis intended to provide the user with information regarding the acoustic damping properties of the specimen 114, such as a time-energy profile of the elastic or work energy associated with the percussion of the tapping rod 102 against the specimen 114.

Using the exemplary testing parameters set forth above, wherein the tapping rod is configured to impact the specimen 114 sixteen times in four seconds, the duration of each percussion response was approximately 0.6 milliseconds, which corresponds to a vibration loading frequency of approximately 1700 Hz. In other embodiments, the percussion response can be manipulated to simulate different vibration loading frequencies.

Figure 5:
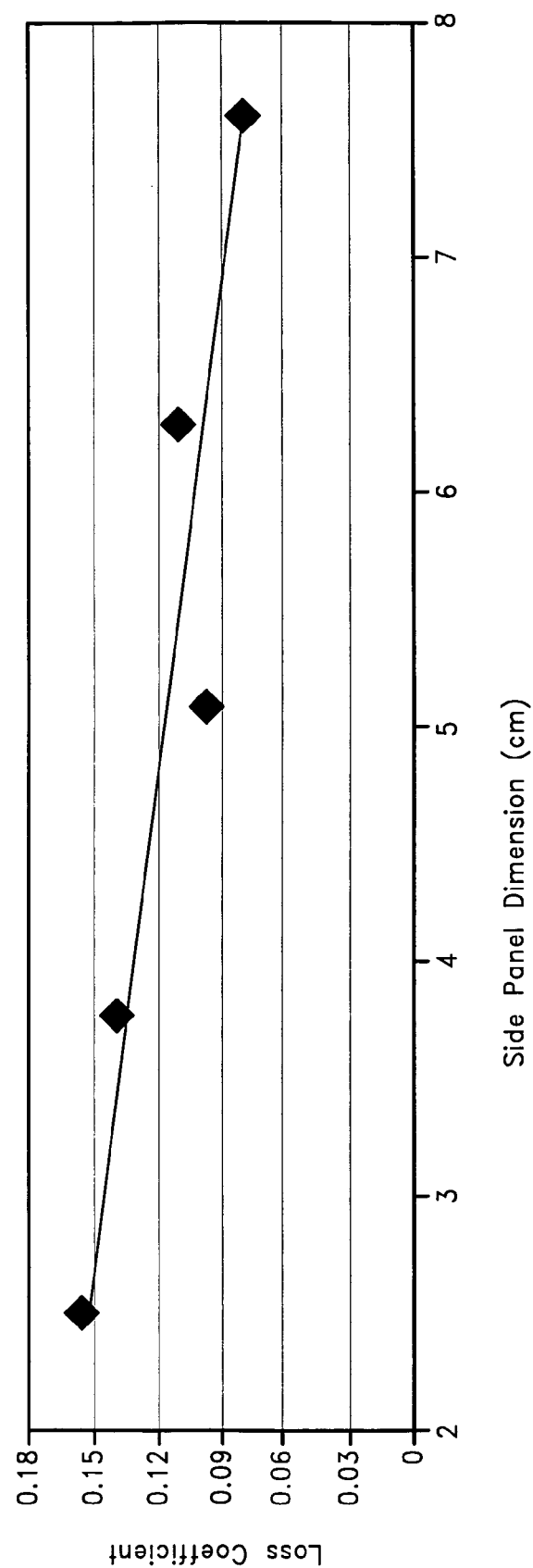
FIG. 5 is a graph of loss coefficient as a function of panel dimension for a panel of damping material.

The percussion instruments described herein can be used with the testing apparatus illustrated in FIG. 4 to characterize the damping characteristics of a wide variety of damping materials, including layered honeycomb materials. For example, relationships between certain properties of the materials and the damping coefficient of the materials can be ascertained. For example, FIG. 5 illustrates the relationship between the dimensions of a substantially square panel having a layered honeycomb structure, and the loss coefficient of the panel. As evident from this graph, smaller panels generally have higher loss coefficients, and thus dissipate the energy of an elastic wave relatively quickly. Conversely, larger panels generally have lower loss coefficients, and thus dissipate the energy of an elastic wave relatively slowly. Therefore, increasing the dimensions of a square panel of damping material decreases the damping effect produced by the panel.

Figure 6:
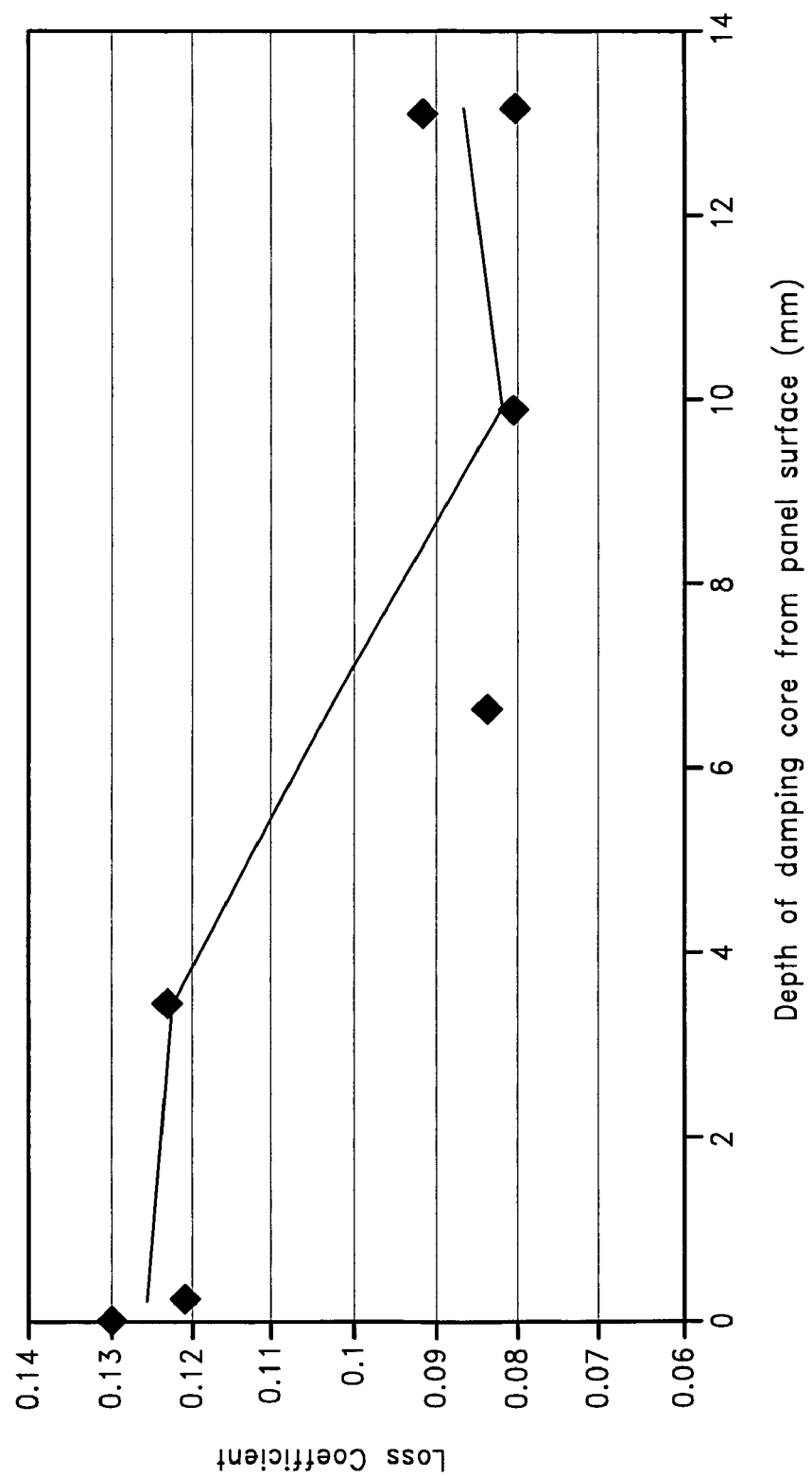
FIG. 6 is a graph of loss coefficient as a function of damping layer depth in a panel of damping material.

As another example, FIG. 6 illustrates the relationship between the depth at which the inner damping core 166 is embedded within the layered honeycomb panel and the loss coefficient of the panel. Generally, the depth at which the inner damping core 166 is embedded within the layered honeycomb panel is the distance between the damping core 166 and the tapping rod 102 impact point. As evident from this graph, panels with deeply embedded damping cores generally have lower loss coefficients, and thus dissipate the energy of an elastic wave relatively slowly. Conversely, panels with shallowly embedded damping cores generally have higher loss coefficients, and thus dissipate the energy of an elastic wave relatively quickly. Therefore, moving the damping core 166 closer to the source of vibrational energy increases the damping effect produced by the damping core 166.

Figure 8:
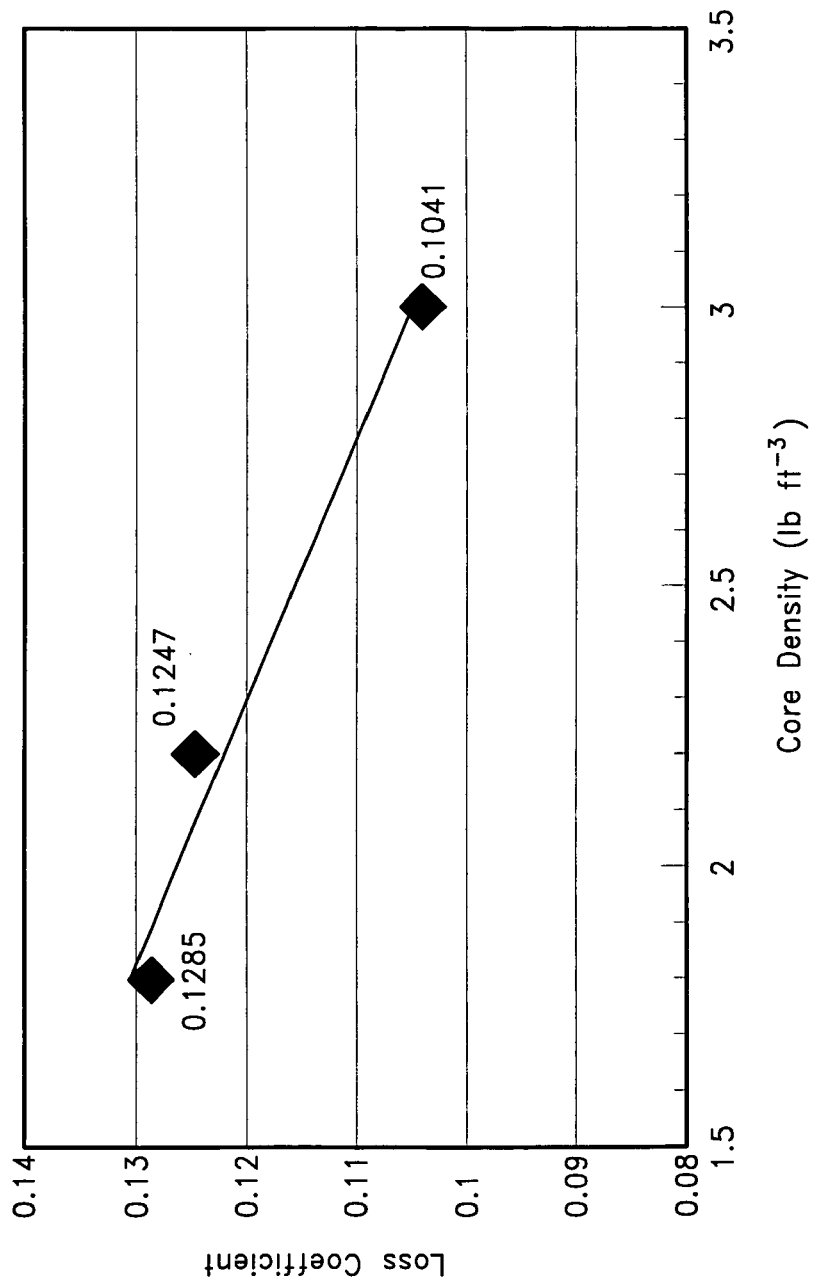
FIG. 8 is a graph of loss coefficient as a function of panel core density for a damping panel having a woven fiberglass core with a phenolic impregnant.
Figure 9:
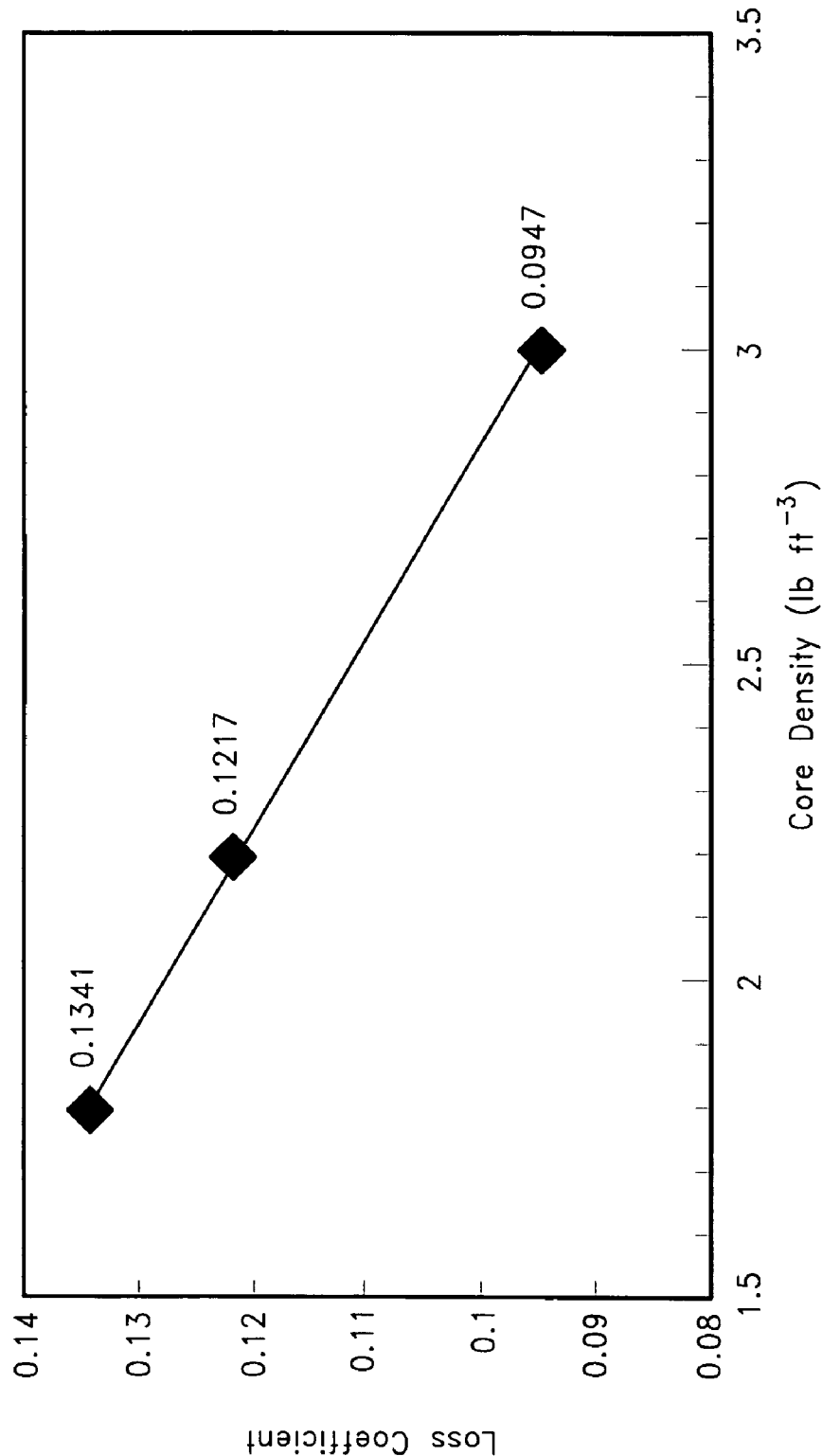
FIG. 9 is a graph of loss coefficient of a function of panel core density for a damping panel having a unidirectional carbon core with a phenolic impregnant.

The damping coefficient can also be affected by the weight density of the core materials disposed within the layers of a composite damping panel, such as the composite panel illustrated in FIG. 7. The loss coefficient of composite panels having varying weight densities can be tested using the apparatus of FIG. 4. For example, FIG. 8 illustrates the relationship between loss coefficient and core weight density for composite damping panels having a 25 mm woven fiberglass core with a phenolic impregnant. Similarly, FIG. 9 illustrates the relationship between loss coefficient and core weight density for composite damping panels having a 25 mm unidirectional carbon core with a phenolic impregnant. As evident from these graphs, panels having an inner core with a greater weight density generally have lower loss coefficients, and thus dissipate the energy of an elastic wave relatively slowly. Conversely, panels having an inner core with a reduced weight density generally have higher loss coefficients, and thus dissipate the energy of an elastic wave relatively quickly. Therefore, decreasing the weight density of the inner core of a damping panel increases the damping effect produced by the panel.

The foregoing provide examples of how a variety of damping panel properties are related to the damping coefficient of such panels. In other embodiments, other properties can be correlated to the panel damping coefficient. Examples of such other properties include, but are not limited to, panel surface area, overall panel thickness, number of layers, and panel composition.

SCOPE OF THE INVENTION

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used in contexts other than evaluation of dental structures.

We claim:

1. A method for assessing the bone density of an anatomical structure, the method comprising:
   tapping the anatomical structure with a tapping rod, thereby imparting mechanical energy to the implant structure;
   measuring, for a time interval, energy reflected from the anatomical structure as a result of the tapping;
   creating a time-energy profile based on the energy reflected from the anatomical structure during the time interval; and
   a shape of evaluating the time-energy profile to determine the bone density of the anatomical structure.

2. A method comprising:
   tapping a dental structure with a tapping rod, thereby imparting mechanical energy to the dental structure, wherein the dental structure is anchored in a foundation having a bone density;
   measuring energy reflected from the dental structure as a result of the tapping;
   creating a time-energy profile of the energy reflected from the dental structure; and
   a shape of evaluating the time-energy profile to make a determination regarding the bone density of the foundation.

3. A method comprising:
   tapping an object that is anchored to an anatomical structure, thereby imparting mechanical energy to the object, wherein the anatomical structure has a bone density;
   measuring energy reflected from the object as a result of the tapping;
   creating a time-energy profile of the energy reflected from the object; and
   a shape of evaluating the time-energy profile to make a determination regarding the bone density of the anatomical structure to which the object is anchored.

4. The method of claim 3, wherein the object is a natural tooth that has been subjected to a trauma-induced fracture.

5. The method of claim 3, wherein the object is a natural tooth that has become at least partially abscessed.

6. The method of claim 3, wherein the object is a natural tooth that has undergone a bone augmentation procedure.

7. The method of claim 3, wherein the object is a dental implant.

8. The method of claim 3, wherein the object is an orthopedic implant.

* * * * *

UNITED STATES PATENT AND TRADEMARK OFFICE
CERTIFICATE OF CORRECTION

PATENT NO. : 7,008,385 B2  
APPLICATION NO. : 10/802117  
DATED : March 7, 2006  
INVENTOR(S) : James C. Earthman et al.

It is certified that error appears in the above-identified patent and that said Letters Patent is hereby corrected as shown below:

Title Page, Item (56)  
At Page 2, Column 1 (Other Publications), Line 22, delete "Assited Protheses"" and insert --Assisted Prosthesis"--, therefor.

Title Page, Item (56)  
At Page 2, Column 2 (Other Publications), Line 14, delete "Manufacuring" and insert --Manufacturing--, therefor.

At Column 1, Line 12, after "disclosure of" delete "both" and insert --all--, therefor.

At Column 1, Line 44, delete "17." and insert --η.--, therefor.

At Column 4, Line 51, delete "17." and insert --η.--, therefor.

At Column 5, Line 57, delete "17," and insert --η,--, therefor.

At Column 7, Line 13, delete "Prosthetic" and insert --prosthetic--, therefor.

At Column 10, Line 37, Claim 1, delete "a shape of evaluating" and insert --evaluating a shape of--, therefor.

At Column 10, Line 48, Claim 2, delete "a shape of evaluating" and insert --evaluating a shape of--, therefor.

At Column 10, Line 60, Claim 3, delete "a shape of evaluating" and insert --evaluating a shape of--, therefor.

Signed and Sealed this

Seventeenth Day of October, 2006

JON W. DUDAS  
*Director of the United States Patent and Trademark Office*